United States Patent [19]
Jones et al.

[11] Patent Number: 5,888,939
[45] Date of Patent: *Mar. 30, 1999

[54] COMPOSITIONS AND METHODS FOR CONTROLLING THE GROWTH OF MICROBIALS IN AQUEOUS MEDIA

[75] Inventors: Ronald Lee Jones, Norcross; Henry Daniel Caughman, Lithonia; Susan M. Shelor, Stone Mountain; Ellwood LeRoy Lines, Jr., Atlanta, all of Ga.

[73] Assignee: Bio-Lab, Inc., Decatur, Ga.

[ * ] Notice: The term of this patent shall not extend beyond the expiration date of Pat. No. 5,591,692 and Pat. No. 5,670,451.

[21] Appl. No.: 935,227

[22] Filed: Sep. 22, 1997

Related U.S. Application Data

[60] Continuation of Ser. No. 695,123, Aug. 5, 1996, Pat. No. 5,670,451, which is a division of Ser. No. 355,112, Dec. 13, 1994, Pat. No. 5,591,692, which is a continuation of Ser. No. 069,122, May 28, 1993, abandoned, which is a continuation of Ser. No. 755,822, Dec. 6, 1991, abandoned.

[51] Int. Cl.$^6$ ............... A01N 43/34; A01N 59/00
[52] U.S. Cl. ............................ 504/155; 504/151
[58] Field of Search .................. 504/155, 151; 424/661, 665; 514/241, 788, 779

[56] References Cited

U.S. PATENT DOCUMENTS

| | | | |
|---|---|---|---|
| 2,789,078 | 4/1957 | Trusler | 424/358 |
| 2,863,800 | 12/1958 | Gottfried | 514/389 |
| 2,988,471 | 6/1961 | Fuchs et al. | 424/661 |
| 3,165,521 | 1/1965 | Slezak et al. | 71/67 |
| 3,187,004 | 6/1965 | Slezak et al. | 548/304 |
| 3,201,311 | 8/1965 | Antonides et al. | 514/241 |
| 3,342,674 | 9/1967 | Kowalski | 514/241 |
| 4,780,216 | 10/1988 | Wojtowicz | 424/661 |
| 5,000,869 | 3/1991 | Dittert | 252/174.13 |
| 5,015,643 | 5/1991 | Jones et al. | 424/661 |

*Primary Examiner*—José G. Dees
*Assistant Examiner*—Alton Pryor
*Attorney, Agent, or Firm*—Woodard, Emhardt, Naughton Moriarty & McNett

[57] ABSTRACT

Compositions and methods are disclosed for sanitizing aqueous media, which combine a chlorine-source composition and a glycoluril-source composition. The compositions are added together or separately, continuously or periodically, and by any of a variety of methods. The glycoluril compound stabilizes the chlorine and prolongs its useful life as a microbicidal agent.

17 Claims, 6 Drawing Sheets

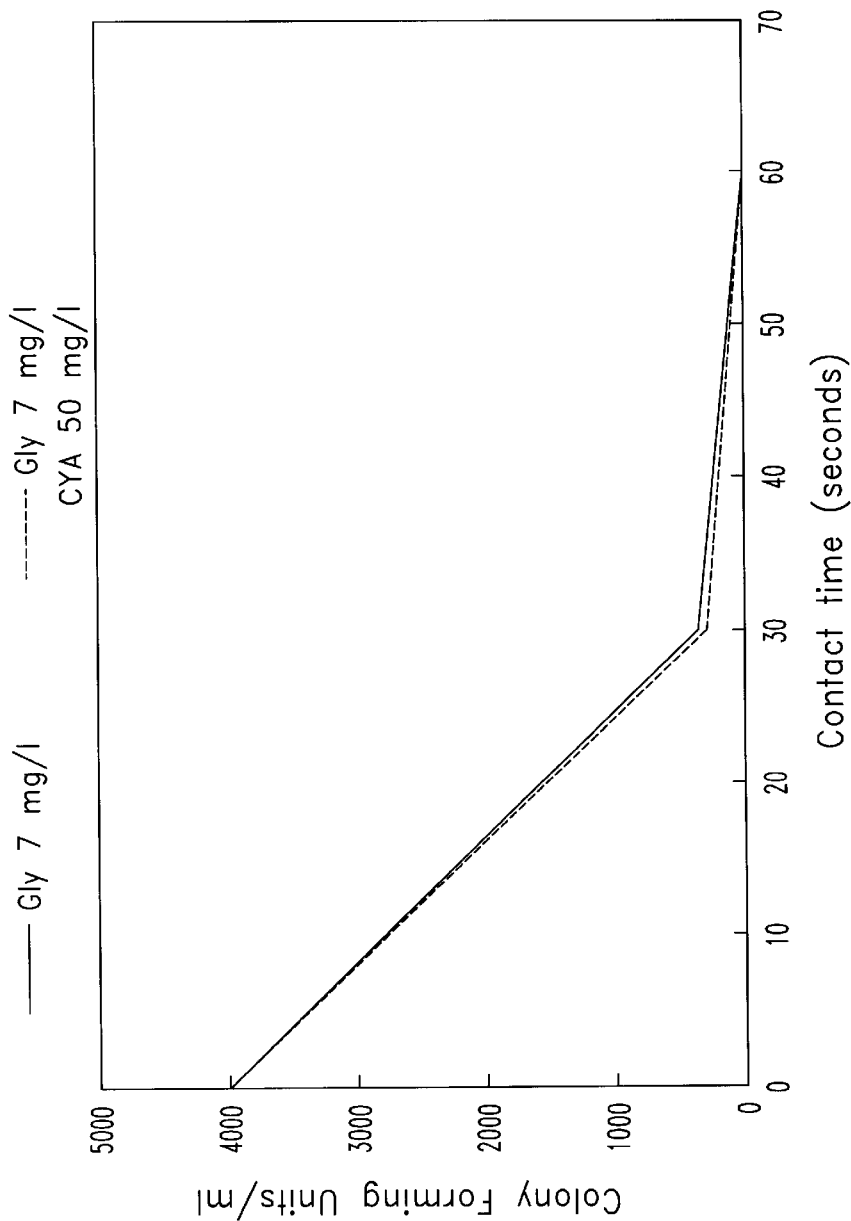

COMPOSITIONS AND METHODS FOR CONTROLLING THE GROWTH OF MICROBIALS IN AQUEOUS MEDIA

This application is a continuation of Ser. No. 695,123, now U.S. Pat. No. 5,670,451, originally filed Aug. 5, 1996, which is a divisional of Ser. No. 355,112, now U.S. Pat. No. 5,591,692, originally filed Dec. 13, 1994, which is a continuation of Ser. No. 08/069,122, filed May 28, 1993, now abandoned, which is a continuation of Ser. No. 07/755,822, filed Sep. 6, 1991, now abandoned.

BACKGROUND OF THE INVENTION

1. Field of the Invention

The present invention relates to the field of disinfectant systems for swimming pool and spa water, cooling tower water, and other aqueous media. More particularly, the invention relates to systems utilizing chlorine as a disinfectant, and to compositions and methods for stabilizing and increasing the useful life of the chlorine in such systems.

2. Description of the Prior Art

The steady increase in the number of swimming pools in use each year has given rise to the need for a more effective, safe, and convenient chemical sanitation. Chlorine in various forms in the most widely used chemical for this purpose, since it is both economical and also highly effective in bacteria and algae control. However, its efficiency and effectiveness vary, and depend upon the method used to introduce the element into the pool water and the type of chlorine compound used. Gaseous chlorine, hypochlorites, and chlorinated organics are all used for swimming pool sanitation and exhibit different types of chlorine residuals and various degrees of bactericidal activity, algicidal activity, and chemical consumption. In addition, such external variables as pool usage and climatic conditions have significant effects upon the efficiency of the sanitizing action.

Various approaches have been proposed in the prior art for stabilizing the chlorine in disinfecting systems. For example, in U.S. Pat. No. 2,988,471, issued to Robert J. Fuchs et al. on Jun. 13, 1961, there is described a method for stabilizing chlorine in aqueous solutions against decomposition by exposure to ultraviolet light or by contact with iron and copper. The method involves adding to the aqueous solution cyanuric acid, ammelide or a salt thereof. The loss of active chlorine is reported to be substantially reduced when the weight concentration of the cyanuric acid is greater than the weight concentration of the available chlorine. The use of cyanuric acid to substantially reduce the loss of active chlorine in aqueous systems exposed to sunlight, for example in swimming pools, has received wide commercial acceptance. See also, e.g., U.S. Pat. No. 4,187,293, issued to Nelson on Feb. 5, 1980.

Although satisfactory results are achieved with the use of cyanuric acid, serious problems exist. One problem is the relatively short half life of active chlorine when exposed to sunlight. At 50 ppm cyanuric acid, the chlorine half-life is only seven hours. On a normal sunny day the majority of the chlorine sanitizer is depleted rapidly.

A second problem that exists is the build up of cyanuric acid in the aqueous system. It is recommended that atypically high concentration of cyanuric acid be reduced to below 100 ppm by partial drainage of the pool water and refilling with fresh water. In fact, in commercial pool operations some health officials will close a pool if the cyanuric acid exceeds 70 ppm. *Kirk-othmer Encyclopedia of Chemical Technology,* 3rd Ed. Vol. 24, p. 430.

In contrast to the present invention, halogenated glycolurils have been proposed in the prior art as the source of disinfecting chlorine. For example, in U.S. Pat. No. 3,165,521, issued to Slezak et al. on Jan. 12, 1965, a method for sanitizing aqueous water systems is disclosed in which haloglycolurils are used as the source of free chlorine to function as a swimming pool sanitizer. The amount of compound used is that which provides satisfactory disinfecting levels of residual chlorine, i.e. about 0.4 to 0.8 ppm. The use of haloglycolurils as the sanitizing agent in swimming pools is also disclosed in U.S. Pat. No. 3,165,521, issued to Lezak. The use of polyhaloglycolurils for controlling algae in water is disclosed in U.S. Pat. No. 3,252,901, issued to Zettler. The use of chlorinated glycolurils in the treatment of sewage is disclosed in U.S. Pat. No. 3,445,383, issued to Horvath et al.

The preparation of glycoluril is disclosed in U.S. Pat. No. 2,731,472, issued to Reibnitz. U.S. Pat. No. 3,071,591, issued to Paterson, discloses a method for the preparation of N-halogenated glycolurils containing both bromine and chlorine for use as disinfecting agents.

Various other sanitizing approaches have involved the use of certain substituted glycolurils. The use of substituted glycolurils in combination with trichlorocyanuric acid and sodium stearate in sanitizing sticks is disclosed in U.S. Pat. No. 3,342,674, issued to Kowalski. The use of chlorinated glycolurils in combination with a metallic hypochlorite in treating sewage is disclosed in U.S. Pat. No. 3,629,408, issued to Horvath. U.S. Pat. No. 3,187,004, issued to Slezak, discloses the synthesis of alkyl and aryl substituted glycolurils and their use in sanitizing swimming pools. This patent discloses the use of N-halogenated glycolurils with alkaline metal salts.

While these various approaches to sanitizing swimming pool water and the like have been proposed in the prior art, there has remained a substantial need for improved compositions and methods providing sustained disinfection of aqueous media. Though many in the past have pursued chlorine-based systems, the useful life of chlorine in such systems has remained undesirably short. Viable commercial approaches have not been forthcoming, and theoretical approaches have been abandoned. The present invention satisfies the need for a stable, effective chlorine-based disinfectant system.

BRIEF DESCRIPTION OF THE DRAWINGS

FIG. 6 shows the efficacy of 1.5 mg/l TAC in the presence of 7 mg/l glycoluril with and without cyanuric acid.

SUMMARY OF THE INVENTION

Figure 1:
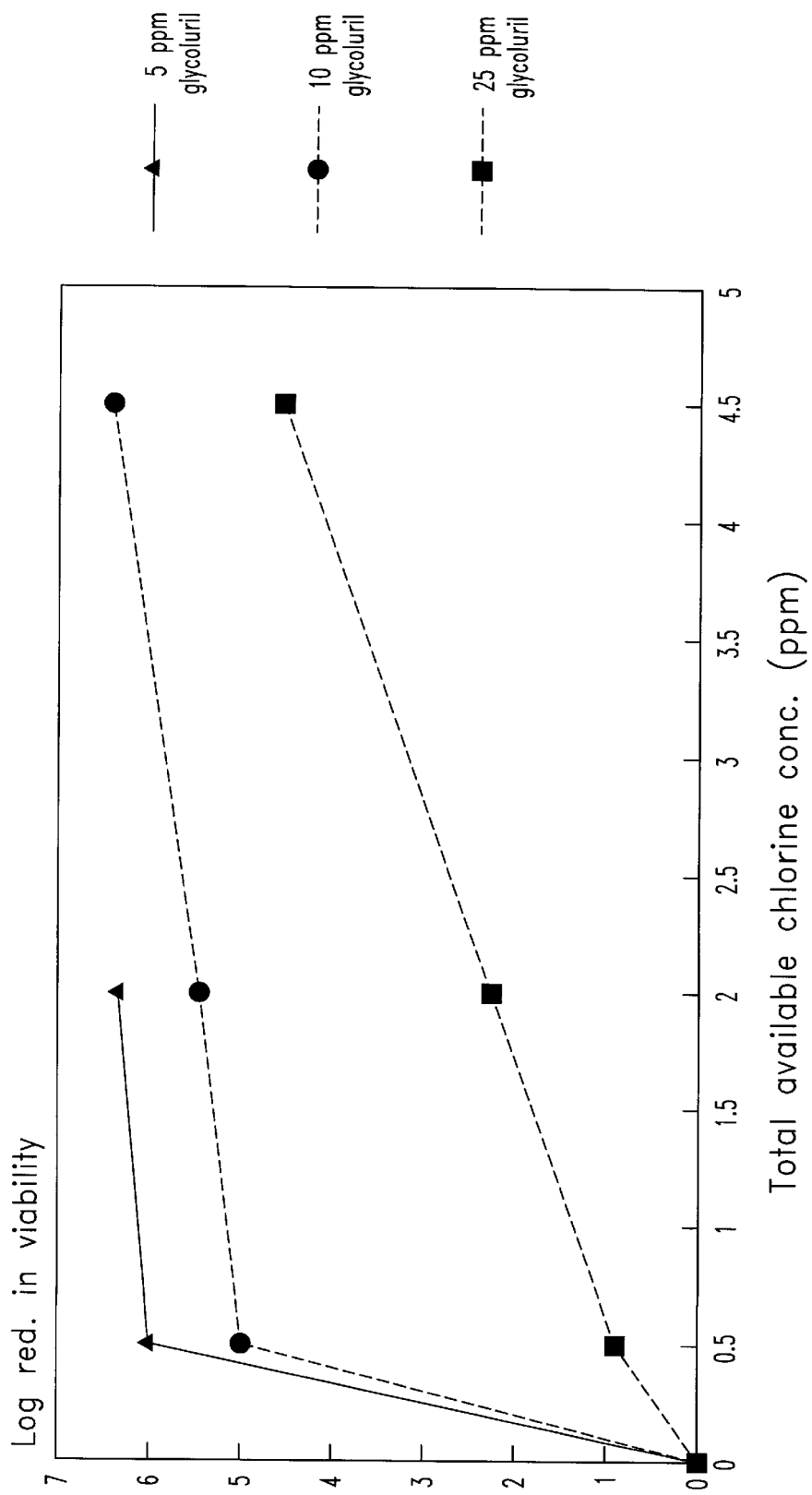
FIG. 1 shows the effect of glycoluril on TCCA at 2 min. contact time.

It is an aspect of the present invention that glycoluril has been found to stabilize chlorine added for disinfection of an aqueous media, thus prolonging the useful life of the added chlorine compounds. Glycoluril can be added at any time, either before or after the addition of the chlorine-source composition, and is maintained at the level determined to provide a desired stabilizing effect for the chlorine.

Aqueous systems, such as swimming pool water, operated on treatment programs based on this disclosure allow for efficient use of the chlorine sanitizer by substantially increasing the chlorine half-life. Several advantages are thereby obtained. Cost savings are realized because the swimming pool water will consume up to 50% less chlorine in a normal pool season. In addition, the reduction of the amount of chlorine consumed will reduce the build up of certain chemicals, such as cyanuric acid, associated with the use of particular chlorine-source compositions, for example trichloro-s-triazinetrione (TCCA).

Controlling the level of the chlorine-source composition and glycoluril in the ranges taught in this disclosure allows for the operation of a very effective treatment program for aqueous systems.

Further objectives of the present invention include providing compositions and methods for reducing the presence of trihalomethanes and the offensive odoring associated with certain chlorine-source compositions, such as TCCA.

DESCRIPTION OF THE PREFERRED EMBODIMENT

For the purpose of promoting an understanding of the principles of the invention, reference will now be made to the preferred embodiment of the invention and specific language will be used to describe the same. It will nevertheless be understood that no limitation of the scope of the invention is thereby intended, such alterations, modifications and further applications of the principles of the invention being contemplated as would normally occur to one skilled in the art to which the invention relates.

The use of chlorine as a disinfectant for swimming pool water, cooling tower water and other aqueous media has been well known for many years. In these environments, chlorine compounds are continuously or periodically added to the water to maintain a microbicidal concentration of chlorine. Without periodic addition, the effective chlorine concentration in the water will decrease due to dissipation, reaction, conversion into unusuable forms, etc. In accordance with past methods, the useful life of added chlorine has been undesirably short, and there has remained an unsatisfied need for extending the effective life of added chlorine compounds.

The present invention provides compositions, systems and methods for extending the useful life of chlorine provided to aqueous media for disinfecting purposes. In particular, the present invention utilizes the activity of glycoluril as a stabilizer for chlorine in an aqueous environment. Addition of the glycoluril and chlorine compositions may be at the same or different times, continuous or periodic, and by any of a variety of addition methods. The presence of the glycoluril at a stabilizing concentration suited to the chlorine concentration will result in an extended effective life for the chlorine in a state suitable for microbicidal activity. For example, the half-life for trichloro-s-triazinetrione (TCCA) in a given system is about 6–7 hours, whereas use of glycoluril in the system extends the half-life to about 25 hours.

The present invention utilizes a glycoluril-source composition that provides glycoluril to stabilize and prolong the useful life of the chlorine. Glycoluril-source compositions useful with the present invention include any which will contribute a glycoluril compound compatible with and useful for stabilizing the chlorine, and suitable for the aqueous media being treated. Substitution on the glycoluril is not critical, provided that the substituents do not interfere with the utility of the glycoluril in the manner described herein.

As used herein, the term "glycoluril" encompasses a compound which includes the basic formula:

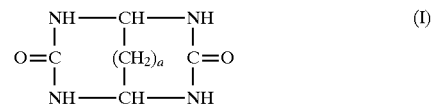

in which a is either 0 or 1. In addition to the unsubstituted glycoluril (I), useful glycoluril-source compositions include the chloro, alkyl and phenyl substituted glycolurils. The term glycoluril thus includes compounds of the foregoing basic structure (I), as well as compounds including substituents such as alkyl, phenyl and chloro groups at available bonding sites. Bromo-substituted glycolurils may also be useful in certain applications, although the presence of the bromine substituent may interfere in some systems with the utility of the glycoluril as a chlorine stabilizer.

More specifically, preferred glycoluril-source compositions include glycolurils having the following structure:

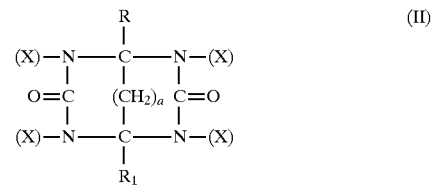

in which R and $R_1$ are independently selected from the group consisting of hydrogen, lower alkyl radicals of from 1 to 4 carbon atoms, and phenyl; each X is either hydrogen, chlorine or bromine; and a is either 0 or 1. It is preferred that R and $R_1$ be either hydrogen or methyl, as alkyl radicals with longer carbon lengths render the glycolurils less soluble in water.

The chlorine concentration in the aqueous media may be obtained from any suitable source when provides hypochlorous acid (HOCl) to the water. Chlorine-source compositions may include both inorganic and organic materials. Useful inorganic materials include molecular chlorine, lithium hypochlorite (LiOCl), calcium hypochlorite (Ca(OCl)$_2$, sodium hypochlorite (NaOCl) and hypochlorous acid (HOCl). Organic sources may include, for example, bromochlorodimethylhydantoin (BCDMH), dichlorodimethylhydantoin (DCDMH) or compositions based on cyanuric acid, such as sodium or potassium dichloro-s-triazinetrione or trichloro-s-triazinetrione (TCCA). These compounds are readily available in commercial form. TCCA, for example, is available from several different suppliers, including Monsanto Chemical Co. under the name ACL-90. The most preferred composition is TCCA. However, it will be appreciated that the chlorine source is not critical to the present invention, provided that the source is compatible with the aqueous media system being treated and is stabilized by the glycoluril compound which is utilized.

A wide variety of aqueous media may be treated by the present invention. In general, any aqueous media which is effectively treated with chlorine, and which is compatible with the described chemicals, can be treated. Typical systems for which the present invention is useful include swimming pools, spas, hot tubs and health related baths, decorative fountains, recirculating water cooling systems, dehumidifier systems, ponds, reservoirs and waste water systems.

The concentrations of glycoluril and chlorine will vary depending on the aqueous media being treated. An advantage of the present invention is that the level of glycoluril can be readily matched to the desired chlorine concentration effective for the given aqueous system. The selected glycoluril level will facilitate maintaining the desired microbicidal level of the chlorine in the water.

The appropriate concentrations of the chlorine, and therefore of the glycoluril, will also differ based upon the conditions attendant to the aqueous media. For example, effective levels may differ based upon such factors as the extent and nature of microbicidal activity needed, the presence of other treatment chemicals, and conditions of use such as temperature, amount of sunlight, pH and the like. Generally, any factors which will affect the stability of the chlorine will have an impact on the desired glycoluril levels. The present invention contemplates that the desired level of chlorine and of glycoluril can be readily determined by one of ordinary skill in the art without undue experimentation, and specific concentrations therefore are not specified herein for each of the variety of treatable aqueous systems.

The level of glycoluril in the water is that which provides an effective concentration of glycoluril to usefully stabilize the chlorine present in the system. Typical concentrations of glycoluril effective as described will range from about 0.1 to about 40.0 ppm of glycoluril in the water. More preferably, the glycoluril is present in the water at from about 1.0 to about 10.0 ppm, with 3.0–7.0 ppm being most preferred for many applications.

In some instances, it may be desirable to provide levels of glycoluril as high as 100 ppm, such as upon initial treatment of a pool. In this way, the level of glycoluril would remain at an effective level for a prolonged period of time. Such high levels of glycoluril may also be used in combination with particularly high levels of chlorine in the water.

The concentration of the chlorine in the water is that which provides an effective level of chlorine for the degree of microbicidal activity desired for the given aqueous media. The term total available chlorine is used herein to include both free chlorine and combined chlorine. Typically, a suitable concentration of total available chlorine will be in excess of about 1.0 ppm, and preferably will range from 1.0 to about 5.0 ppm in the water. This is true, for example, in the case of swimming pool water. By way of comparison, the desired total available chlorine level in cooling tower water may differ, ranging from about 1.0 to about 1.0 ppm of total available chlorine.

The present invention advantageously uses two separate compositions, one primarily providing the chlorine and the other primarily providing the glycoluril. The overall effect is that the glycoluril is maintained at a level which stabilizes the chlorine and prolongs its life to reduce the amount and frequency of addition of the chlorine. Although certain forms of glycoluril-source compositions may include chlorine which will be contributed to the water, such forms of glycoluril are contemplated in the present invention as primarily stabilizing compositions. Indeed, the amount of chlorine which can be added to the water through a chlorinated form of glycoluril is typically either insufficient, or would require the use of amounts of chlorinated glycoluril which are otherwise undesirable.

The glycoluril and chlorine compositions may be administered to the aqueous media in any manner effective to provide the desired concentrations of each compound. The glycoluril and chlorine may be added to the water either together or separately, and either periodically or continuously. The methods of application may vary with the aqueous systems being treated, and the conditions of use pertinent thereto. In general, however, the methods are restricted only by the need to maintain effective levels of the glycoluril and chlorine as described, and may be any suited to the physical forms and particular compounds employed. Existing disinfectant systems using chlorine contemplate various methods for maintaining a desired level of the chlorine in an aqueous system. The present invention is advantageous in that it may be readily adapted for use with a wide variety of such existing water treatment systems.

Typical methods of addition known in the art are broadcast and erosion methods. Broadcasting refers to a direct addition of the chemical to the aqueous media in solid, typically granular, or liquid form. Compositions useful in the present invention may be readily prepared in forms and concentrations convenient for broadcast application.

In the erosion method, compositions are fabricated into a solid-form material which is contained with the water in a manner to effect a relatively slow erosion of the solid material, thus gradually releasing the composition into the water. The composition to be added is formed or compressed into solid forms, such as tablets, sticks, pucks and other shapes, typically by a hydraulic or mechanical press. The solid-form materials may include inert fillers, such as sodium chloride or boric acid, that assist in the tabletting process. The solid material may also contain other ingredients such as tabletting aids, e.g., mold release agents, binders, corrosion inhibitors, scale inhibitors and other components known to those skilled in the art.

Erosion methods are commonly employed in the prior art for introducing chlorine-source compositions into swimming pools, for example. The chlorine composition, in solid form, is placed into a release device through which water is circulated to erode the solid material. In the case of a swimming pool, the tablet, stick or puck can be placed into a skimmer basket, in-line or off-line feeders, or a floating release device. While erosion may also be used for the glycoluril, it has been found that at least certain forms and types of glycoluril are not well suited to introduction by continuous erosion methods, because for these forms the erosion method provides insufficient levels of glycoluril in the water.

The glycoluril-source and chlorine-source compositions may be provided either as two separate materials or as a physically combined product, depending on the form and intended manner of addition of the products. The provision of separate materials is preferred since the preparation of the compositions is thereby made simpler. Also, the methods and compounds for adding the chlorine and the glycoluril are more flexible, for example permitting the use of liquid chlorine with a granular glycoluril composition, or permitting the continuous erosion addition of the chlorine and a periodic broadcasting of the glycoluril composition. The separate addition further enables the user to independently control the concentrations of the two compounds, which will be particularly useful if the water conditions result in a disparate depletion of one compound compared to the other.

One particular method of maintaining the desired levels of chlorine and glycoluril is to provide a continuous addition of chlorine to the water, coupled with a periodic broadcast addition of the glycoluril compound. Additive glycoluril-source compositions can be readily formulated to provide the desired levels of glycoluril in water upon addition of prescribed amounts of material at indicated time intervals.

For example, granular forms of the compositions may be readily prepared which give desired concentrations of glycoluril when added to the water at intervals ranging from daily to every week or two. Naturally, the frequency of addition will depend on the conditions to which the water is subjected, and also on the amount, concentration and type of glycoluril-source composition being added.

In a particular embodiment, the foregoing method may be enhanced by using as the chlorine source a mixture of a chlorine compound and a glycoluril compound in a physical combination which facilitates sustained release of the chlorine compound into the water. Thus, a tablet or stick form of chlorine-source material may be formulated which also includes a percentage of glycoluril. The glycoluril is formulated with the chlorine-source compound in the solid tablet or stick because it has been found that this will slow the erosion rate for the solid material. This in turn extends the life of the solid material and reduces the frequency with which the tablets or sticks need to be replaced. Consequently, the chlorine is added to the aqueous system at a controlled and uniform rate over a longer period of time. The tablet in this method will also contribute a certain amount of glycoluril to the water, but the desired level of glycoluril may not be primarily obtained from this source. Instead, a glycoluril-source compound is also otherwise added into the water, such as by periodic broadcasting, to bring up and maintain the level of glycoluril in the water as desired.

According to this particular approach, the solid form tablets or sticks are formulated to include both chlorine and glycoluril source compounds. The chlorine compound is preferably selected from the group consisting of calcium hypochlorite, lithium hypochlorite, sodium dichloro-s-triazinetrione, potassium dichloro-s-triazinetrione, and trichloro-s-triazinetrione, and is present in an amount of from about 50.0% to about 99.99% by weight. The glycoluril-source composition is preferably selected from the group consisting of glycoluril, alkyl-substituted glycoluril, phenyl-substituted glycoluril, and chloro-substituted glycoluril, and is present in an amount of from about 0.01% to about 50.0% by weight. Further discussion of such compositions and their advantages is contained in the copending U.S. patent application, Ser. No. 652,983, filed Feb. 11, 1991, and hereby incorporated by reference.

In accordance with this method, a particular embodiment of the solid-form chlorine material comprises approximately 50–99.99% by weight of trichloro-s-triazinetrione and 0.01–50% by weight of glycoluril. In a related embodiment, the solid-form material includes approximately 50–99.9% by weight of trichloro-s-triazinetrione, 0.01–50% by weight of glycoluril and 0–20% by weight of an alkali bromide salt. A preferred composition is 80–98% trichloro-s-triazinetrione (TCCA) and 2–20% glycoluril, or 70–90% trichloro-s-triazinetrione (TCCA), 5–10% sodium or potassium bromide salt, and 5–20% glycoluril. Another preferred mixture is 75–90% trichloro-s-triazinetrione, 5–10% potassium bromide and 5–20% glycoluril. The preferred glycolurils are unsubstituted glycoluril (I) and the chloroglycolurils, such as dichloroglycoluril and tetrachloroglycoluril. For most applications, glycoluril is preferred.

By way of particular example, the present invention is well suited to use in the treatment of swimming pool water. Current systems provide for the addition of chlorine to maintain certain accepted levels, typically 1 to 5 ppm of total available chlorine in the water. The present invention may be directly adapted for use in the variety of prior art systems which utilize chlorine as a disinfectant by maintaining in such systems that indicated levels of glycoluril effective to stabilize the chlorine. The glycoluril also may be used with various other treatment chemicals typically used in such systems, such as algicides, clarifiers and the like.

In addition, it is a feature of the present invention that the compositions may be readily formulated to adapt their use in swimming pool and other water systems. Swimming pool chemicals, for example, are typically constituted to require the addition of convenient, prescribed amounts on a periodic basis, usually weekly. The chemicals utilized in the present invention can be formulated on this basis. More preferably, the present invention prolongs the useful life of the chlorine to the point that the frequency of addition of chemicals may be extended beyond the usual weekly basis, perhaps to once every two weeks or longer.

In a typical swimming pool application, the present invention would proceed as follows. About every week the user employs a prescribed amount of solid-form, chlorine-source tablets or sticks in an erosion device. Coupled with this is the periodic addition of the glycoluril-source composition, also preferably at weekly intervals. The presence of the glycoluril prolongs the useful life of the chlorine, reducing the frequency with which chlorine would otherwise have to be added.

In an alternate method, the solid-form material includes the chlorine-source composition and glycoluril, for example about 95% TCCA and about 5% glycoluril. This formulation has a slowed erosion rate compared to prior art chlorine products, and therefore will last up to two weeks or more. The stabilizing of the chlorine effected by the glycoluril matches well with the extended erosion life of these alternate tablets or sticks.

In addition, other chemicals may be used at the same time. In particular, it may be desirable to perform periodic "shocking" of swimming pool or other water, a common step in prior art procedures. In this case, the shock may be conveniently performed, for example every two weeks, by adding a conventional material, such as sodium dichlorocyanurate, at the same time as the addition of the glycoluril. A full pool treatment system would then only require the addition of algicide, such as a quaternary ammonium compound, at the same two week interval, thus providing the user with a convenient system and method for the treatment of swimming pool water.

It has been observed that the ratio of glycoluril to total available chlorine can be selected to optimize the duration and microbicidal efficacy of the chlorine. The amount of glycoluril in the water is preferably limited to an extent appropriate to result in sufficient hydrolyzing of the chlorine. It is possible that the presence of too much glycoluril in comparison to the amount of total available chlorine will affect the amount of chlorine in solution, and therefore the microbicidal activity. In a sense, the glycoluril can be present in such high amounts relative to the chlorine that the chlorine is made so stable as to reduce its microbicidal activity. For example, a standard hypochlorite solution will effectively kill $10^6$ bacteria in about 30 seconds. A ratio of glycoluril to total available chlorine of about 5:1 will result in a kill of about half of the bacteria in about two minutes, and higher ratios will further delay the kill time. Therefore, although water systems having higher ratios of glycoluril to total available chlorine will still have microbicidal efficacy, the performance will be diminished. It has been found that preferred ratios of total available chlorine to glycoluril are from about 10:1 to about 1:10, more preferably about 5:1 to about 1:5. While increased stability of chlorine is normally associated with decreased microbicidal activity, the present invention provides increased stability and desired microbicidal activity.

The present invention is useful in a wide variety of applications. A person skilled in the art can readily determine the suitability of given chlorine-source and glycoluril-source compositions for a particular aqueous system. The present invention may also be used in conjunction with a variety of other chemicals such as algicides, fungicides, clarifiers, pH adjusters, sequesterants and the like, and may be used with other chlorine stabilizers such as cyanuric acid, oxazolidinone, imidazolidinone, dimethylhydantoin, succinimide, toluenesulfonamide, sulfonamidobenzoic acid, melamine, dioxohexahydrotriazine, piperazinedione, and azodicarbonamidine.

In addition to the stabilization of chlorine, the present invention has also been found to provide several ancillary benefits to the aqueous systems. For example, the addition of glycoluril in the amount indicated reduces the offensive chloramine odor associated with certain chlorinating systems, such as those using TCCA. Similarly, the development of trihalomethanes is diminished in the presence of the glycoluril.

The following examples further illustrate the present invention, and are provided as exemplary but not restrictive as to the scope of the present invention.

EXAMPLE 1

This example illustrates a method for treatment of water systems in accordance with the present invention. This experiment was conducted to demonstrate the rate of loss of chlorine from solutions containing cyanuric acid, glycoluril and mixtures of the two. This experiment was conducted under controlled conditions designed to simulate conditions expected while operating a pool under full sunlight.

Four liter beakers containing 3500 mls of distilled water were placed in a Revco environment chamber equipped with a special ultra violet lamp that emits UV radiation at 295–340 nm. It is known that chlorine is degraded by sunlight in the region of 295–340 nm. The water was balanced to the following specifications:

Calcium Hardness 200–250 ppm
Total Alkalinity 100–135 ppm
pH 7.2–7.4

The test chemicals were then added as shown in Table I below:

TABLE I

Test Chemical Systems

| Beaker #1 | Cyanuric Acid (CYA) (PPM) | Glycoluril (G) (PPM) |
|---|---|---|
| 1 | 10 | 0 |
| 2 | 50 | 0 |
| 3 | 0 | 5 |
| 4 | 0 | 10 |
| 5 | 0 | 20 |
| 6 | 50 | 5 |
| 7 | 10 | 5 |
| 8 | 50 | 10 |
| 9 | 10 | 10 |
| 10 | 50 | 20 |
| 11 | 10 | 20 |

The chlorine source for this study was trichloro-s-triazinetrione (TCCA). The chlorine demand on the test systems was met by adding excess chlorine and allowing the water to circulate overnight. The total available chlorine level was adjusted the next morning with the TCCA stock solution.

The study was conducted over a 24 hour period, during which the beakers were stirred continuously. The test solutions were exposed to the ultraviolet radiation at 295–340 NM. The air and water temperatures were controlled at 80°–85° F., and the relative humidity at 80–100%. Water samples were taken and the total available chlorine was measured using a HACH 3000 spectrophotometer and DPD colorimetric method. Due to the large number of beakers involved, the study was conducted in two runs.

TABLE II

Test Data - Run #1

| Beaker # | 1 | 2 | 3 | 4 | 5 |
|---|---|---|---|---|---|
| CYA/G (ppm) | 10/0 | 50/0 | 0/5 | 0/10 | 0/20 |
| Time | $TCl_2$ | $TCl_2$ | $TCl_2$ | $TCl_2$ | $TCl_2$ |
| Initial | 1.80 | 1.78 | 1.79 | 1.82 | 1.80 |
| 1 hr | 1.36 | 1.48 | 1.65 | 1.68 | 1.67 |
| 2 hr | 1.08 | 1.25 | 1.54 | 1.56 | 1.53 |
| 3 hr | 0.93 | 1.15 | — | — | — |
| 9 hr | 0.25 | 0.66 | 1.26 | 1.31 | 1.31 |
| 19 hr | 0.09 | 0.27 | 0.95 | 1.01 | 1.01 |
| 24 hr | 0.06 | 0.15 | 0.80 | 0.87 | 0.89 |

TABLE III

Test Data - Run #2

| Beaker # | 6 | 7 | 8 | 9 | 10 | 11 |
|---|---|---|---|---|---|---|
| CYA/G (ppm) | 0/5 | 10/5 | 50/10 | 10/10 | 50/20 | 10/20 |
| Time | $TCl_2$ | $TCl_2$ | $TCl_2$ | $TCl_2$ | $TCl_2$ | $TCl_2$ |
| Initial | 1.50 | 1.51 | 1.52 | 1.53 | 1.60 | 1.5 |
| 2 hr | 1.27 | 1.38 | 1.36 | 1.43 | 1.45 | 1.4 |
| 5 hr | 1.15 | 1.24 | 1.29 | 1.31 | 1.34 | 1.3 |
| 21 hr | 0.89 | 0.82 | 0.94 | 0.98 | 0.98 | 0.9 |
| 24 hr | 0.61 | 0.80 | 0.88 | 0.91 | 0.90 | 0.9 |

The objective of this study was to determine the rate of loss of total available chlorine ($TCl_2$) from water systems containing cyanuric acid, glycoluril and mixtures of the two, when exposed to ultraviolet light in the wavelength region of 295–340 nm. The chlorine half-life was determined by plotting % remaining total available chlorine ($TCl_2$) vs. time (hours). As shown in TABLE IV, water systems containing both cyanuric acid and glycoluril exhibited a greater half-life than water systems that contained only cyanuric acid, i.e., the residual total available chlorine is dissipated more slowly in water systems containing a combination of cyanuric acid and glycoluril. Therefore, the chlorine is available for a longer period of time, and its bactericidal and disinfecting activity is more continuously effective.

TABLE IV

Chlorine Half-life

| Beaker #1 | CYA (ppm) | Glycoluril (ppm) | t ½ (hrs) |
|---|---|---|---|
| 1 | 10 | 0 | 5.0 |
| 2 | 50 | 0 | 7.0 |
| 3 | 0 | 5 | 22.0 |
| 4 | 0 | 10 | 24.0 |
| 5 | 0 | 20 | 25.0 |
| 6 | 50 | 5 | 29.0 |
| 7 | 10 | 5 | 27.0 |
| 8 | 50 | 10 | 33.0 |
| 9 | 10 | 10 | 35.0 |
| 10 | 50 | 20 | 32.0 |
| 11 | 10 | 20 | 35.0 |

EXAMPLE 2

Solutions comprising 1 ppm, 2.5 ppm, and 5 ppm total available chlorine from TCCA, and glycoluril concentrations of 5, 10 and 25 ppm, were tested for biocidal activity. These compositions were added to [test microbes] and [kill rate] was measured. As shown in FIG. 1, each of the chlorine concentrations had greater biocidal activity at lower glycoluril concentrations. Additionally, the rate of biocidal activity in the solution of 25 ppm glycoluril was slower than the rates at 5 and 10 ppm glycoluril.

EXAMPLE 3

This example examines the potential for glycoluril to build-up through normal swimming pool usage. A 20,000 gallon vinyl in-ground pool was filled with water and balanced to the following specifications:

Calcium Hardness: 175 ppm

Total Alkalinity: 125 ppm pH: 7.4

CYA: 35 ppm

The pool was maintained at 1 to 3 ppm total available chlorine using compressed, one-half pound TCCA sticks, and was shocked biweekly using lithium hypochlorite to bring the total available chlorine level to 8 ppm.

During the eight month test period the glycoluril level ranged from 1 to 5 ppm. A sum of 1125 grams of glycoluril was added to the pool during the test period. At the end of the test period less than 1 ppm of glycoluril was measured in the water.

EXAMPLE 4

This Example illustrates the ability of glycoluril to reduce the volatility of chlorine and inorganic chloramines from aqueous systems, thereby reducing the offensive odors caused by the compounds. The results indicate that the glycoluril appears to effectively retard the loss of free chlorine and inorganic chloramines from aqueous systems.

Figure 2:
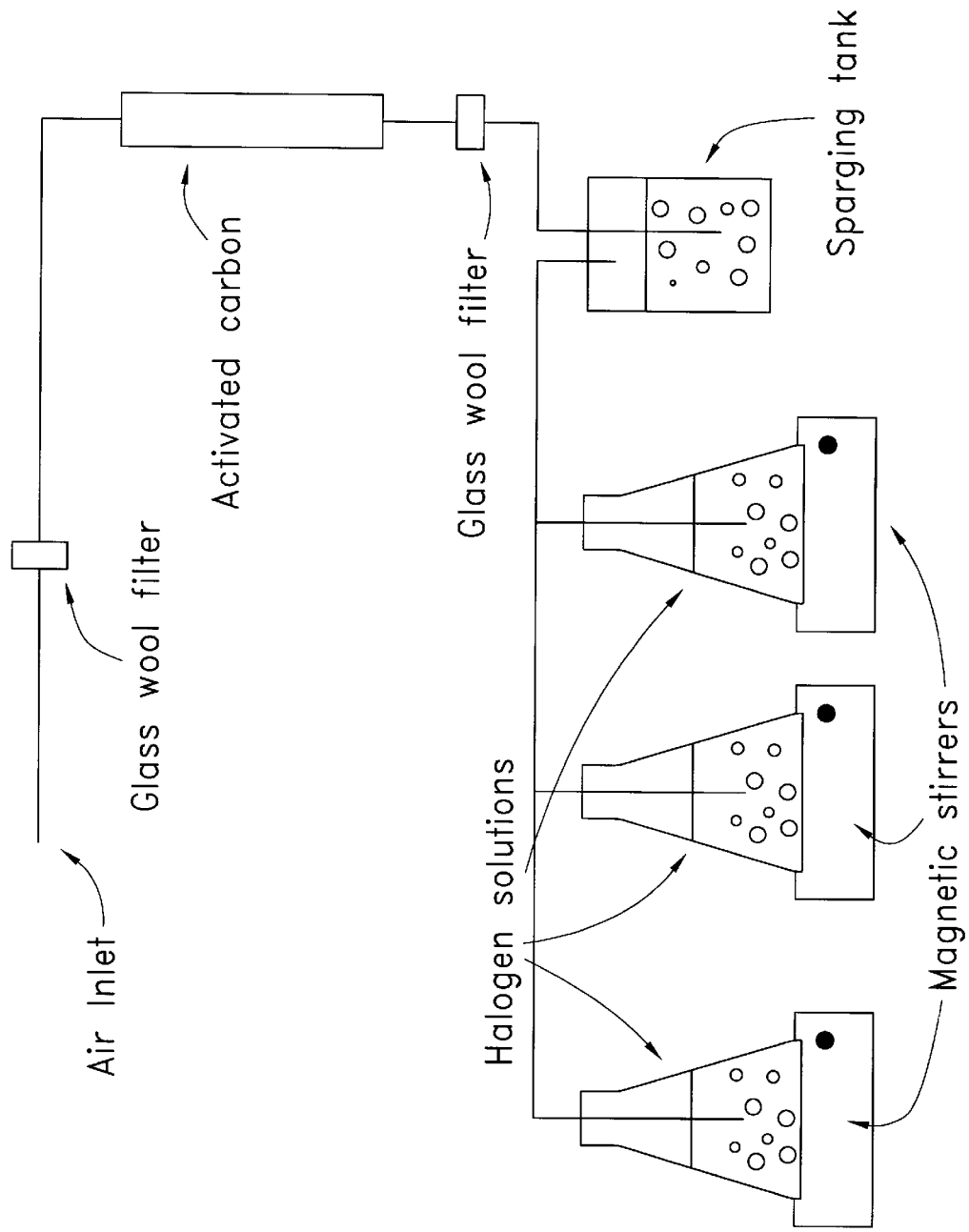
FIG. 2 shows an airstripping apparatus constructed to determine the effect of glycoluril upon the volitility of chlorine and chloroamines.

To determine the effect of glycoluril upon the volatility of chlorine and chloramines, the airstripping apparatus shown in FIG. 2 was constructed. Air was initially passed through a wad of glass wool to trap solid particles, as well as oil droplets. Next, the air went through a column filled with activated carbon to further clean the air stream. After the carbon filter, another glass wool wad trapped any carbon particles that may have escaped the column. Sequential filtering such as this has been previously shown to generate halogen demand free air.

Demand free air was channeled into a sparging tank filled with demand free water. Air leaving the tank should have been saturated with water. This water rich air was used to strip chlorine from the solutions used in the subsequent experiments. It was necessary to use water saturated air for these experiments to minimize evaporative losses in the flasks containing the halogen solutions. Moreover, to increase the effect of the air stripping action, magnetic stirrers were used to continually agitate the solutions.

Figure 3:
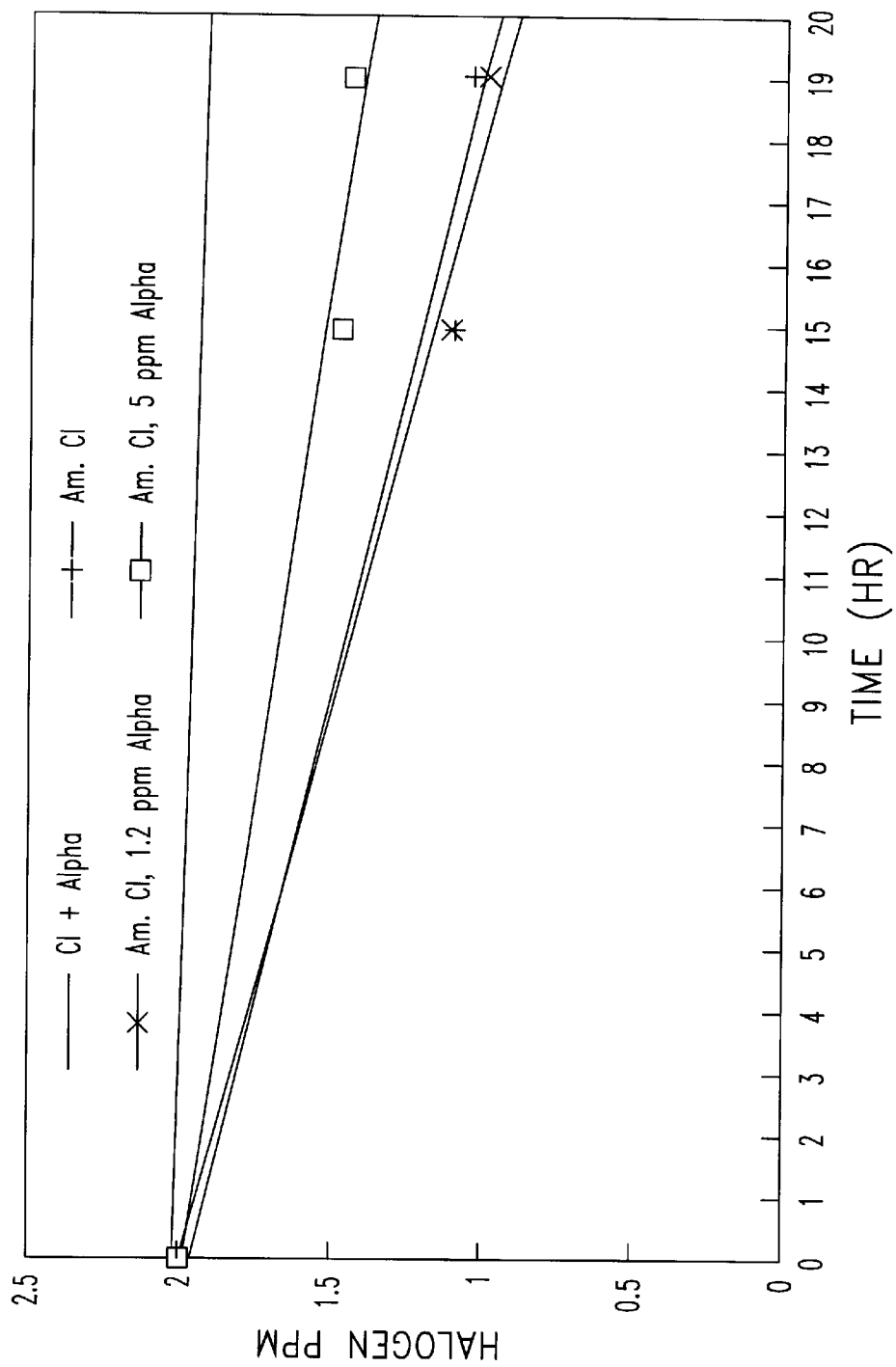
FIG. 3 shows the effect of glycoluril on chlorine volitization after ammonium chloride was subsequently added to a glycoluril and chlorine mixture.

Chlorine was dosed into erlenmeyer flasks containing one liter of demand free water (18 megohm resistance) at a concentration of 2 ppm. Ammonium chloride concentration was 2 ppm. Glycoluril was added to give a final concentration of 1.2 or 5 ppm. Flask 1 contained chlorine and 5 ppm glycoluril, flask 2 contained chlorine and the ammonium salt, flask 3 contained chlorine, the ammonium salt and 1.2 glycoluril, and flask 4 contained chlorine, the ammonium salt and 5 ppm glycoluril. In flasks 3 and 4, the ammonium chloride was added after the addition of the chlorine and glycoluril. The results are contained in Table V and FIG. 3.

TABLE V

| Flask | Total Halogen ppm |
|---|---|
| Time = 0 | |
| 1 | 2.01 |
| 2 | 1.96 |
| 3 | 2.00 |
| 4 | 1.99 |
| Time = 15 hr | |
| 1 | 1.96 |
| 2 | 1.16 |
| 3 | 1.10 |
| 4 | 1.46 |
| Time = 19 hr | |
| 1 | 1.90 |
| 2 | 1.03 |
| 3 | 0.98 |
| 4 | 1.43 |

Figure 4:
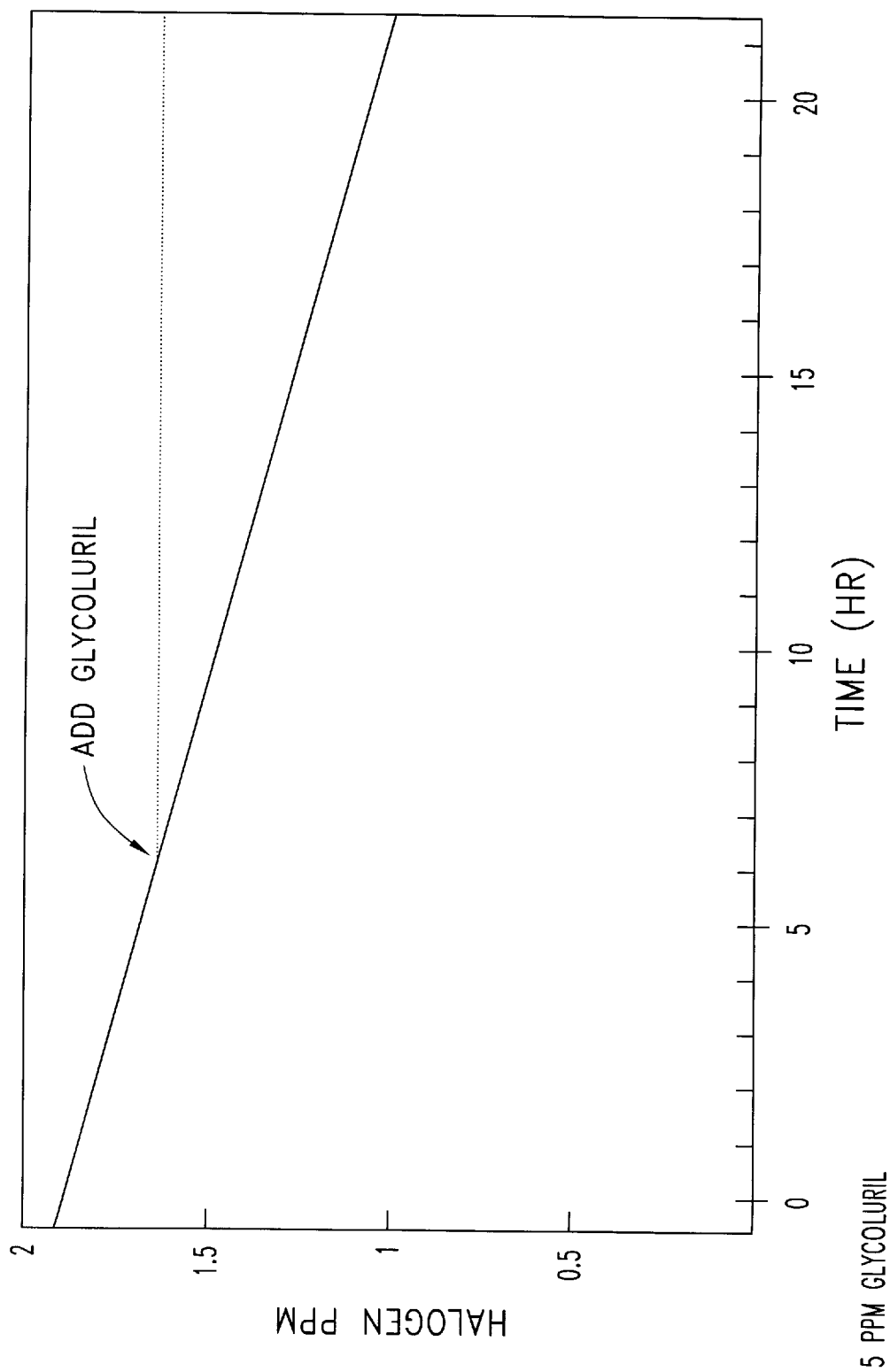
FIG. 4 shows the effects of addition of unsubstituted glycoluril on chlorine volitization.

Adding glycoluril to Flask 1 decreased the volatility of chlorine. Referring to FIG. 4, the solid line shows the first 6 hours of data extrapolated to the 21st hour. This approximates the rate of volatilization of chlorine under experimental conditions. The dashed line demonstrates the effect of glycoluril. Glycoluril was added at the sixth hour and chlorine flashoff essentially ceased.

EXAMPLE 5

Figure 5:
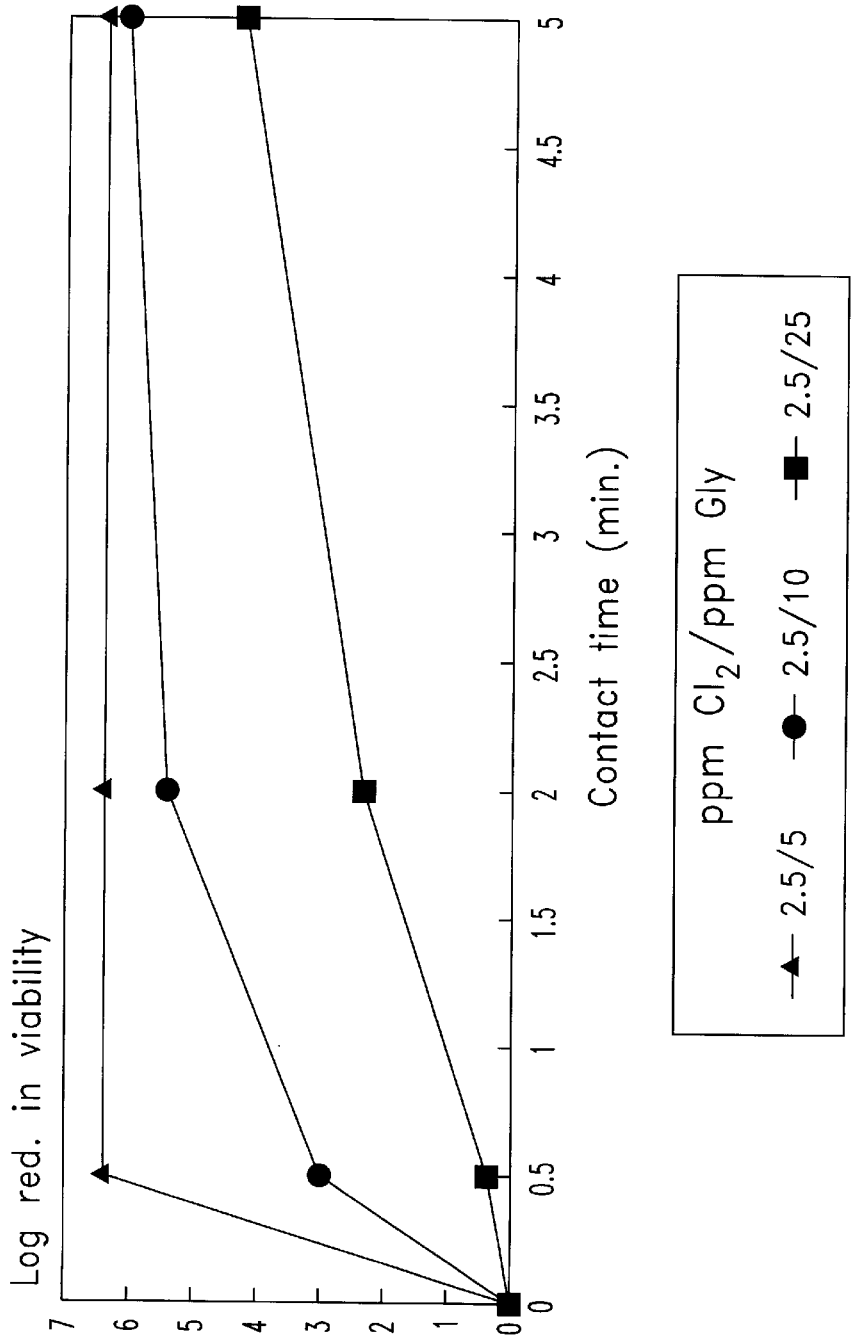
FIG. 5 shows effects of glycoluril on TCCA, 2.5 ppm C12/5, 10, 25 ppm glycoluril.

Aqueous solutions containing 2.5 ppm total available chlorine and 5, 10 and 25 ppm glycoluril were prepared and tested over a period of 5 minutes for microbicidal activity in accordance with the method of Example 2. The results of this test are depicted in FIG. 5, showing that the rate of biocidal activity in the solution of 25 ppm glycoluril is slower than the rate at 5 and 10 ppm glycoluril.

EXAMPLE 6

A further study was conducted to demonstrate the efficacy of chlorine as a disinfectant when stabilized with glycoluril alone or with glycoluril and another chlorine stabilizer. As shown in FIG. 6, a solution containing 1.5 mg/l total available chlorine remains essentially equally efficacious as a disinfectant, whether combined with 7 mg/l of glycoluril alone, or with 7 mg/l glycoluril and 50 mg/l isocyanuric acid (CYA). Glycoluril used in accordance with the present invention at varying concentrations, as previously discussed, is an effective stabilizer for the chlorine disinfectant and the chlorine remains an effective disinfectant, either in the presence or absence of other chlorine stabilizers.

EXAMPLE 7

The following example illustrates the effectiveness of glycoluril to inhibit the formation of trihalomethanes (THM) from humic acid. Test solutions were prepared in 120 ml new vaccine bottles which were washed with chromic acid cleaning solution, rinsed in hot tap water, and then in distilled water before use. The following stock solutions were prepared for use in these tests: a 200 ppm solution of available chlorine from commercial bleach, a 0.1% humic acid solution (Humic acid, sodium salt; Aldrich Chemical Co., Inc., CAS #1415-93-6), a 0.04% glycoluril solution, and a 0.1% s-triazinetrione (CYA) solution. Thirteen solutions were prepared as outlined in Table VI.

TABLE VI

Preparation of Test Solutions

| | | ml of Test Stock Solution | | |
|---|---|---|---|---|
| Bottle | H.A. | Compd. G | CYA | Chlorine |
| 0 | 0.3 | 1.5 | — | 6 |
| 2 | 0.3 | 3.0 | — | 6 |
| 3 | 0.3 | 7.5 | — | 6 |
| 4 | 0.3 | 15.0 | — | 6 |
| 5 | 0.3 | 1.5 | 6 | 6 |
| 6 | 0.3 | 3.0 | 6 | 6 |
| 7 | 0.3 | 7.5 | 6 | 6 |
| 8 | 0.3 | 15.0 | 6 | 6 |
| 9 | 0.3 | — | 6 | 6 |
| 10 | 0.3 | — | 6 | 6 |
| 11 | — | 15.0 | — | 6 |
| 12 | — | — | 6 | 6 |
| 13 | — | — | — | 6 |

Each bottle was ¾ filled with boiled glass distilled water, and the stock solutions were then added thereto. Each bottle was then filled to the top with boiled distilled water, covered with a Teflon cap, and sealed with a metal vaccine crimp cap. The bottles were held at room temperature overnight and the next day were analyzed for the presence of trihalomethanes. The solutions were analyzed for chloroform, bromoform, bromodichloromethane and dibromochloromethane, and the results are shown in Tables VII and VIII.

TABLE VII

Concentrations of Reactants in Solutions and the Resulting ppm Chloroform Assayed in each Solution

| | ml of Test Stock Solution | | | | Results |
|---|---|---|---|---|---|
| Bottle | H.A. | Compd. G | CYA | Chlorine | (ppm CHCl3) |
| 1 | 15 | 5 | — | 10 | 0.015 |
| 2 | 15 | 10 | — | 10 | <0.010 |
| 3 | 15 | 25 | — | 10 | 0.061 |
| 4 | 15 | 50 | — | 10 | 0.102 |
| 5 | 15 | 5 | 50 | 10 | 0.069 |
| 6 | 15 | 10 | 50 | 10 | 0.047 |
| 7 | 15 | 25 | 50 | 10 | 0.030 |
| 8 | 15 | 50 | 50 | 10 | 0.031 |
| 9 | 15 | — | — | 10 | 0.137 |
| 10 | 15 | — | 50 | 10 | 0.081 |
| 11 | — | 15 | — | 10 | 0.088 |
| 12 | — | — | 50 | 10 | 0.059 |
| 13 | — | — | — | 10 | <0.010 |

TABLE VIII

Percent Reduction of Chloroform in Sample Compared to the Control, Solution 9, at 137 ppb

| Bottle | ppb CHCl3 | % Reduction in THM |
|---|---|---|
| 1 15 HA, 5 G | 15 | 89.1 |
| 2 15 HA, 10 G | <10 | >92.7 |
| 3 15 HA, 25 G | 61 | 55.5 |
| 4 15 HA, 50 G | 102 | 25.5 |
| 5 15 HA, 5 G, 50 CYA | 69 | 49.6 |
| 6 15 HA, 10 G, 50 CYA | 47 | 65.7 |
| 7 15 HA, 25 G, 50 CYA | 30 | 78.1 |
| 8 15 HA, 50 G, 40 CYA | 31 | 77.4 |
| 9 positive control | 137 | — |
| 10 15 HA, 50 CYA | 81 | 40.9 |
| 11 50 G | 88 | 35.8 |
| 12 50 CYA | 59 | 56.9 |
| 13 negative control | <10 | >92.7 |

As the data reveals, except for chloroform, the THMs were below the minimum detection level of less than 0.010 ppm in all test solutions. Solution 13 was a negative control, containing only 10 ppm chlorine in boiled distilled water, and it had less than 0.010 ppm chloroform. When CYA alone (#12), glycoluril alone (#11) and CYA plus glycoluril together (#10) were added to the chlorine solution, there were increases in chloroform to 59, 88 and 81 parts per billion (ppb), respectively. This indicated that available chlorine reacted with these compounds or impurities in these compounds to form some chloroform. The addition of only humic acid to the chlorine solution (#9) gave the highest reading for chloroform of 137 ppb, and acted as the positive control.

Solutions 1–4 represented varying concentrations of glycoluril in combination with 15 ppm humic acid and chlorine. The results indicate that 5 and 10 ppm glycoluril almost completely prevented chloroform formation, while 25 ppm only inhibited formation by 55.5%, and 50 ppm glycoluril only results in 25.5% reduction over the positive control. It is therefore shown that low levels of glycoluril (5 and 10 ppm) prevent chloroform formation from humic acid almost completely, while higher concentrations inhibit THM formation but to a lesser extent. These results are explainable on the assumption that the impurity in the glycoluril resulted in the formation of the chloroform. At 5 and 10 ppm levels, the impurity was too low to form an appreciable amount of chloroform, while at the higher concentrations there was sufficient impurities to appreciably affect the test. In any event, the tests do demonstrate the effectiveness of glycoluril to prevent or inhibit the formation of THMs.

Solutions 5–8 represent varying levels of glycoluril with 50 ppm CYA. This treatment group gave good reduction over the positive control, and the results were consistent with varying concentrations of glycoluril. There was some slight chloroform inhibition at 5 ppm glycoluril and greater inhibition at 10, 25 and 50 ppm glycoluril in combination with the CYA. Maximum inhibition was reached at 25 ppm, with no improvement at 50 ppm. Thus, the optimum glycoluril range is in the range of 10–25 ppm.

This test amply demonstrates a definite reduction of chloroform from the reaction of chlorine with humic acid when the treatment group contained both CYA and gycoluril. There was about 41% reduction by 50 ppm CYA alone, but as high as 78% reduction was found with combinations of CYA and glycoluril. The combination of CYA and glycoluril was more effective at low concentrations than either compound by itself.

What is claimed is:

1. A method for disinfecting an aqueous system which comprises:
    (a) maintaining in the aqueous system a disinfecting concentration of total available chlorine; and
    (b) adding to the aqueous system an amount of a glycoluril-source composition sufficient to maintain a concentration in the aqueous system of from about 0.1 to about 40.0 ppm of glycoluril.

2. The method of claim 1 and which comprises maintaining a concentration of from about 1.0 to about 10.0 ppm of glycoluril.

3. The method of claim 1 in which the glycoluril-source composition has the formula:

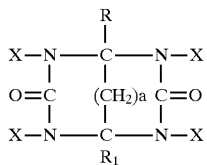

in which R and $R_1$ are independently selected from the group consisting of hydrogen, lower alkyl radicals of from 1 to 4 carbon atoms, and phenyl; X is either hydrogen or a halogen; and a is either 0 or 1.

4. The method according to claim 3, wherein at least 1 X is bromo.

5. The method according to claim 3, wherein at least 1 X is chloro.

6. The method of claim 1 and which comprises maintaining in the aqueous system a concentration of at least about 0.6 ppm of total available chlorine.

7. The method of claim 5 and which comprises maintaining between about 1.0 and about 10.0 ppm of glycoluril in the aqueous system.

8. The method of claim 7 and which comprises maintaining between about 1 and about 5 ppm of total available chlorine in the aqueous system.

9. The method of claim 1 and which further includes adding to the aqueous system a chlorine stabilizer in addition to the glycoluril-source composition, the additional stabilizer being selected from the group consisting of cyanuric acid, oxazolidinone, imidazolidinone, dimethylhydantoin, succinimide, toluenesulfonamide, sulfonamidobenzoic acid, melamine, dioxohexahydrotriazine, piperazinedione and azodicarbonamidine.

10. The method of claim 1 in which said chlorine-source composition comprises a composition selected from the group consisting of: calcium hypochlorite, sodium hypochlorite, lithium hypochlorite, sodium dichloro-s-triazinetrione, chlorine gas, potassium dichloro-s-triazinetrione, trichloro-s-triazinetrione, bromochlorodimethylhydantoin, dichlorodimethylhydantion and hypochlorous acid.

11. A disinfecting composition, comprising a mixture of:
(a) 50 to 99.99% by weight of a chlorine-source material; and
(b) 0.01 to 50% by weight of glycolurils having the formula:

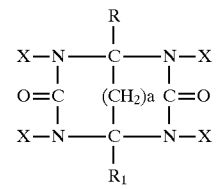

in which R and $R_1$ are independently selected from the group consisting of hydrogen, lower alkyl radicals of from 1 to 4 carbon atoms, and phenyl; X is either hydrogen or a halogen; and a is either 0 or 1.

12. The composition according to claim 1 wherein at least 1 X is bromo.

13. The composition according to claim 1 wherein at least 1 X is chloro.

14. The composition according to claim 13 wherein said chlorine-source material and said glycolurils are jointly provided as a physically combined product.

15. The composition according to claim 14 wherein said physically combined product is provided as a tablet or a stick.

16. The composition according to claim 13 wherein said composition comprises about 95% chlorine-source material and about 5% glycolurils.

17. The composition according to claim 1 wherein said chlorine-source material is trichloro-s-triazinetrione.

* * * * *

UNITED STATES PATENT AND TRADEMARK OFFICE
CERTIFICATE OF CORRECTION

PATENT NO. : 5,888,939
DATED : March 30, 1999
INVENTOR(S) : Ronald Lee Jones; Henry Daniel Caughman; Susan M. Shelor; and Ellwood LeRoy Lines, Jr.

It is certified that error appears in the above-identified patent and that said Letters Patent is hereby corrected as shown below:

In column 1, line 26, please change "in" to --is--.
In column 4, lines 42, please change "when" to --which--.
In column 6, line 21, please change "contained" to --contacted--.
In column 8, line 1, please change "that" to --the--.
In column 13, TABLE VI, under "Bottle", please change "0" to -- 1 --.
In column 13, TABLE VI, under "CYA" line 9, please change "6" to -- -- --.
In column 16, line 24, please change "claim 1" to --claim 11--.
In column 16, line 26, please change "claim 1" to --claim 11--.
In column 16, line 37, please change "claim 1" to --claim 11--.

Signed and Sealed this

Tenth Day of October, 2000

Attest:

Q. TODD DICKINSON

*Attesting Officer*                   *Director of Patents and Trademarks*